US008648029B2

(12) United States Patent
Corominas (10) Patent No.: US 8,648,029 B2
(45) Date of Patent: Feb. 11, 2014

(54) COMPOSITION COMPRISING A DIESTER QUATERNARY AMMONIUM FABRIC SOFTENER WITH DURABLE PEARLESCENT AESTHETICS

(75) Inventor: Francesc Corominas, Grimbergen (BE)

(73) Assignee: The Procter & Gamble Company, Cincinnati, OH (US)

( * ) Notice: Subject to any disclaimer, the term of this patent is extended or adjusted under 35 U.S.C. 154(b) by 424 days.

(21) Appl. No.: 12/255,966

(22) Filed: Oct. 22, 2008

(65) Prior Publication Data

US 2009/0156455 A1 Jun. 18, 2009

(30) Foreign Application Priority Data

Oct. 29, 2007 (EP) .................................... 07119473

(51) Int. Cl.
*C11D 1/62* (2006.01)

(52) U.S. Cl.
USPC ........... 510/515; 510/276; 510/287; 510/308; 510/322; 510/329; 510/330; 510/394; 510/504

(58) Field of Classification Search
USPC ......... 510/276, 287, 308, 322, 329, 330, 394, 510/504, 515
See application file for complete search history.

(56) References Cited

U.S. PATENT DOCUMENTS

| 3,256,180 | A | | 6/1966 | Weiss |
| 3,606,989 | A | * | 9/1971 | Park .................. 8/108.1 |
| 3,974,076 | A | * | 8/1976 | Wiersema et al. ............. 510/524 |
| 4,839,084 | A | * | 6/1989 | Ouhadi et al. ................. 510/338 |
| 4,892,673 | A | * | 1/1990 | Dixit et al. .................... 510/338 |
| 5,004,556 | A | * | 4/1991 | Julemont et al. ............. 510/304 |
| 5,019,376 | A | | 5/1991 | Uick |
| 5,064,544 | A | * | 11/1991 | Lin et al. ........................ 510/521 |
| 5,176,713 | A | * | 1/1993 | Dixit et al. ........................ 8/137 |
| 5,185,088 | A | * | 2/1993 | Hartman et al. .............. 510/515 |
| 5,205,837 | A | | 4/1993 | Andrean et al. |
| 5,501,806 | A | * | 3/1996 | Farooq et al. ................. 510/522 |
| 5,792,219 | A | * | 8/1998 | Hartman et al. ................... 8/137 |
| 6,267,810 | B1 | | 7/2001 | Pfaff et al. |
| 6,511,705 | B1 | * | 1/2003 | Jetzer et al. .................... 427/209 |
| 2003/0095944 | A1 | * | 5/2003 | Midha ........................ 424/70.27 |
| 2003/0162689 | A1 | * | 8/2003 | Schymitzek et al. .......... 510/515 |
| 2003/0215415 | A1 | * | 11/2003 | Mitsumatsu et al. ....... 424/70.27 |
| 2004/0005285 | A1 | * | 1/2004 | Midha ........................ 424/70.27 |
| 2004/0014627 | A1 | * | 1/2004 | Adams et al. ................. 510/329 |
| 2004/0092419 | A1 | * | 5/2004 | Connor et al. ................. 510/327 |
| 2004/0092424 | A1 | * | 5/2004 | Boutique et al. .............. 510/466 |
| 2004/0097396 | A1 | * | 5/2004 | Peeters et al. ................. 510/515 |
| 2004/0110648 | A1 | * | 6/2004 | Jordan et al. .................. 510/101 |
| 2004/0132699 | A1 | * | 7/2004 | Zhuang et al. ................. 514/170 |
| 2005/0022312 | A1 | | 2/2005 | Bigorra Llosas et al. |
| 2005/0130874 | A1 | * | 6/2005 | Demeyere et al. ............ 510/522 |
| 2006/0079438 | A1 | | 4/2006 | Brush et al. .................... 510/516 |
| 2006/0252668 | A1 | * | 11/2006 | Frankenbach et al. ........ 510/504 |
| 2007/0014823 | A1 | * | 1/2007 | Iwata ............................. 424/401 |
| 2007/0225424 | A1 | | 9/2007 | Schulz et al. |
| 2008/0063619 | A1 | * | 3/2008 | Olsen et al. ............. 424/70.122 |
| 2008/0119383 | A1 | * | 5/2008 | Boardman et al. ............ 510/521 |
| 2008/0263780 | A1 | | 10/2008 | Declercq et al. |
| 2009/0069207 | A1 | * | 3/2009 | Panandiker et al. .......... 510/296 |
| 2009/0186797 | A1 | * | 7/2009 | Panandiker et al. .......... 510/296 |
| 2009/0209445 | A1 | * | 8/2009 | Panandiker et al. .......... 510/296 |
| 2009/0318595 | A1 | * | 12/2009 | Steinmetz et al. ............. 524/195 |
| 2011/0281785 | A1 | * | 11/2011 | Gizaw et al. .................. 510/516 |
| 2012/0036651 | A1 | * | 2/2012 | Frankenbach et al. ............ 8/137 |

FOREIGN PATENT DOCUMENTS

| EP | 0 581 193 A2 | 2/1994 |
| EP | 0 181 773 B2 | 1/1999 |
| GB | 2 187 197 | 9/1987 |
| JP | 60 038308 A | 2/1985 |
| JP | 60 038309 A | 2/1985 |
| WO | WO 2004/014321 A3 | 2/2004 |
| WO | WO 2007/100669 A1 | 9/2007 |

OTHER PUBLICATIONS

International Search Report Dated Feb. 23, 2009—4 pgs.

* cited by examiner

*Primary Examiner* — Charles Boyer
(74) *Attorney, Agent, or Firm* — James F. McBride; David V. Upite (57) ABSTRACT

The present invention relates to liquid compositions provided with durable pearlescent appearance, and to a process of producing said compositions.

15 Claims, 1 Drawing Sheet

COMPOSITION COMPRISING A DIESTER QUATERNARY AMMONIUM FABRIC SOFTENER WITH DURABLE PEARLESCENT AESTHETICS

FIELD OF THE INVENTION

The present invention relates to liquid compositions provided with durable pearlescent appearance, and to a process of producing said compositions.

BACKGROUND OF THE INVENTION

Compositions having pearlescent or pearl-like appearance are widely known in the art. Not only cosmetic and personal care compositions, but also detergent and fabric treatment compositions are sometimes imparted with pearlescent aesthetics so as to render the resulting compositions more attractive, valuable and rich-like to the consumers. Typically, such compositions are provided with the desired pearlescence by the introduction of pearlescent additives which can e.g. take the form of pearlescent particles (WO 2007/100669), pearlizing waxes (EP-B1-0181773), pearlizing concentrates (WO 2004/014321) or pearlizing dispersions (EP-A2-0581193). The requirement to incorporate pearlescent additives may undesirably increase formulation complexity and lead to substantial additional costs for the overall product formulation. Additionally, the introduction of those additives may sometimes adversely affect the stability of the resulting formulations due to incompatibility with other ingredients, and may cause losses of performance.

Notwithstanding the benefits and advantages associated with the pearlescent compositions disclosed in the art, there is still a need for liquid pearlescent compositions having improved formulation simplicity and flexibility, and which overcome the drawbacks associated with the known pearlescent compositions.

It is therefore an objective of the present invention to provide liquid pearlescent compositions possessing improved formulation simplicity and flexibility, while providing unaffected stability upon storage. It has now been found that the above objective can be met by providing compositions according to the present invention.

Advantageously, the compositions according to the present invention may be processed under very low thermal energy requirements, which can be shown by low water temperature. A further advantage associated with the compositions according to the present invention is that they may take the form of creamy, rich-like compositions provided with excellent and durable viscosity characteristics. It is still a further advantage that the compositions according to the present invention provide excellent dispensability and dispersibility properties.

Other advantages and more specific properties of the method according to the present invention will be clear after reading the following description of the invention.

SUMMARY OF THE INVENTION

The present invention relates to a liquid composition having pearlescent aesthetics, wherein the composition comprises a benefit agent in the form of a plurality of particles, wherein at least a portion of said plurality of particles have a sheet-like microstructure and an average size ranging from 0.1 to 50 μm. In another embodiment, the present invention relates to a process of preparing a liquid composition having pearlescent aesthetics, wherein the composition comprises a benefit agent, the process comprising the steps of processing the benefit agent thereby producing a plurality of particles, the particles having a sheet-like microstructure and an average size ranging from 0.1 to 50 μm.

DETAILED DESCRIPTION OF THE INVENTION

Definitions

By "pearlescent", it is meant herein any effect comprising shimmer, brilliance, iridescence, glitter and sparkling. Pearlescent appearance is defined in accordance with Pearlescence Determination as defined herein.

By "additional pearlescing agent", it is meant herein any pearlescent modifying agent other than said particles formed from said benefit agent. Those of skill in the art will understand that additional pearlescing agents include any pearlescing agents known in the art, including but not limited to include inorganic natural substances, such as mica, bismuth oxychloride and titanium dioxide, and organic compounds such as fish scales, metal salts of higher fatty acids, fatty glycol esters and fatty acid alkanolamides.

By "sheet-like microstructure", it is meant herein that the corresponding particles present a microstructure which may look similar to a sheet when seen from the front, i.e. the particles adopt a configuration which is substantially planar and flat such that two dimensions of the particle (length and width) are at least 5 times the third dimension (depth or thickness).

By "benefit agent", it is intended to represent any compound which has any beneficial effect to any animate or inanimate treated surface, such as human or animal body, fabric, hard surfaces, and the like.

Benefit Agent

The composition according to the present invention comprises as one essential ingredient a benefit agent comprising a fabric softening active as defined below. Typically, the compositions according to the present invention comprise from 1% to 30%, preferably from 4% to 25%, more preferably from 5% to 18%, most preferably from 7% to 17% by weight of the composition of said benefit agent, or mixtures thereof. It has surprisingly been found that pearlescent composition appearance can be achieved without additional need for any additional pearlescing agents.

In one preferred embodiment, the benefit agent has a melting point between about 25° C. and about 120° C., alternatively from about 30° C. and about 100° C., alternatively from about 32° C. and about 40° C. Melting point is the temperature range wherein a solid changes physical state from solid to a liquid at standard atmospheric conditions of 1 ATM.

In another embodiment, the benefit agent has a phase transition temperature between about 25° C. and about 100° C., when present in an aqueous solution.

A person skilled in the art will understand that this phase transition can be determined with proper instrumentation, like DSC (Differential Scanning Calorimetry) or micro-DSC, among others. It has importantly been found that by providing a benefit agent having melting point and a phase transition as defined herein, the benefit agent can be subjected to processing conditions such that at least a portion of the benefit agent forms a plurality of particles which provide the desired pearlescent appearance. Without intending to be bound by theory, it is believed that the use of an ultrasonic homogenizer such as the Sonolator® from Sonic Corp. is capable of achieving sufficient high shear to create said plurality of particles from said benefit agent.

It has been found that by providing, as separate feeds, 1) a molten feed stream of said benefit agent at a temperature above said melting point with 2) a cold feed stream comprising water at a temperature below said melting point of said benefit agent, wherein the cold feed stream is at a sufficient flow rate such that at least a portion of said molten feed stream solidifies upon contact; and combining them within a mixing chamber while simultaneously subjecting said combination of feeds with high shear, it is possible to achieve sufficiently small particles having sheet-like structure to provide pearlescent appearance.

Benefit Agent Forming a Plurality of Particles

The composition according to the present invention comprises, as an essential feature, at least a portion of the benefit agent forms a plurality of particles some of them having a sheet-like microstructure and having an average size ranging from about 0.1 to about 50 µm. Preferably, said particles have an average size ranging from about 0.1 to about 40 µm, more preferably from about 0.1 to about 30 µm, most preferably from about 0.1 to about 20 µm, as determined by Dynamic Light Scattering Method as defined herein. As used herein, average size includes average diameter.

In the context of the present invention, it has been indeed surprisingly discovered that the presence a plurality of particles having a sheet-like microstructure and having an average size ranging from 0.1 to 50 µm in a liquid composition, will impart such composition with excellent pearlescent aesthetics. In the context of the present invention, the benefit agent present in the claimed composition will not only provide the expected beneficial effect but will also provide the excellent pearlescent aesthetics. Accordingly, the present invention discloses the first example of a liquid composition comprising a benefit agent, wherein said benefit agent will assume a dual function of providing both the expected beneficial effect and pearlescent aesthetics to said composition. Without wishing to be bound by theory, it is believed that the particular sheet-like microstructure of the particles will allow the light to reflect on the surface of said particles thereby inducing a pearlescent shimmer.

It has been no less surprisingly discovered that the pearlescent aesthetic obtained with the composition according to the present invention is not only maintained upon prolonged storage, but also said pearlescent effect does not detrimentally affect the physical stability of the liquid composition of the present invention upon storage.

Even more, the sheet-like particles help provide the liquid composition with a very high low-shear viscosity and shear thinning rheological profile, which, without willing to be bound by theory, is responsible for the excellent physical stability of the liquid composition. Physical stability is defined by the lack of phase split throughout a large period of time and the maintenance of this shear thinning rheological profile throughout the shelf life time of the liquid composition.

Advantageously, the physical stability of the compositions according to the present invention is not detrimentally affected by the addition of sensitive components such as perfume ingredients or suspended particles. Also, without intending to be bound by theory, it is believed that the nano-sized particles are sufficiently small in size such that the nano-particles tend to resist aggregating over time as compared to conventional liquid compositions which tend to have particles which are non-nano-sized.

Incidentally, it has surprisingly been found that the liquid compositions as disclosed herein exhibit excellent physical stability over time. This excellent stability can be observed by the presence of substantially no phase separation upon prolonged storage at room temperature.

The desired particles having a sheet-like microstructure and having an average size ranging from 0.1 to 50 µm have been achieved by processing the corresponding benefit agent through high energy density technologies which use hydrodynamic and/or ultra-sonic cavitation to create sufficient disruption to create nano-sized particles. These processing steps are described more in details herein below.

In one embodiment of the present invention, from about 0.01%, alternatively from about 0.2%, alternatively from about 0.35%, alternatively from about 0.5% to at least about 50%, alternatively at least about 75%, alternatively at least about 90%, alternatively at least about 95%, alternatively at least about 99%, alternatively at least about 99.9%, by weight of said benefit agent is present as a plurality of particles having a sheet-like microstructure as recited herein. Those skilled in the art will recognize that the benefit agent compound may further be provided in a form comprising vesicles, discs, platelets, lamellar sheets, and mixtures thereof.

In one embodiment, from about 0.01%, alternatively from about 0.2%, alternatively from about 0.35%, alternatively from about 0.5% to at least about 50%, alternatively at least about 75%, alternatively at least about 90%, alternatively at least about 95%, alternatively at least about 99%, alternatively at least about 99.9%, by weight of said benefit agent, are particles having an average size as disclosed herein, i.e. ranging from 0.1 to 50 µm, in accordance with the Dynamic Light Scattering Method. As used herein, average size (which includes average diameter) is in reference to the outer layer of the particles and is determined by the Dynamic Light Scattering Method.

The Dynamic Light Scattering Method measures the average diameter of the particles by light scattering data techniques, which is an intensity-weighted average diameter. One suitable machine to determine the average diameter is a Brookhaven 90Plus Nanoparticle Size Analyzer. A dilute suspension with concentration ranging from 0.001% to 10% v/v using a suitable wetting and/or dispersing agents is prepared. A 10 mL sample of the suspension is placed into a sample cell and measurements are recorded providing average particle diameter.

Additional Pearlescing Agent:

It has importantly been found that the present invention is capable of achieving pearlescent appearance without the need to add any additional pearlescing agents. It has been found that the plurality of particles having the sheet-like microstructure and average size as recited herein provides the desired pearlescent appearance without any need for additional pearlescing agents. Those of skill in the art will understand that although additional pearlescing agent is not needed to provide the desired physical appearance, its exclusion is not necessary. As such, the composition can comprise an additional pearlescing agent at a level of from about 0.01% to about 0.5%, preferably from about 0.01% to about 0.35%, more preferably from about 0.01% to about 0.2% by weight of the composition of additional pearlescing agent.

According to a preferred execution of the present invention, the compositions herein are free or essentially free of additional pearlescing agent. As used herein the term "essentially free" means no intentionally added amount of that ingredient is provided in the composition. In one embodiment, the composition comprises less than about 1%, preferably less than about 0.1%, more preferably less than about 0.01%, even more preferably less than about 0.001%, most preferably about 0% of the additional pearlescing agent, by weight of the liquid composition, yet still achieves the desired Pearlescing Index as defined below.

Fabric Softening Active:

In one preferred embodiment, the composition according to the present invention comprises a benefit agent selected from fabric softening actives (FSA). Suitable fabric softener actives for use herein include, but are not limited to diester quaternary ammonium compounds and dialkyl quaternary ammonium compounds, and mixtures thereof.

Typically, the compositions according to the present invention comprise from about 1% to about 30%, preferably of from about 4% to about 25%, more preferably of from about 5% to about 18%, and most preferably from about 7% to about 17% by weight of the total composition of said fabric softener active, or mixtures thereof.

Diester Quaternary Ammonium (DEQA) Compounds

The diester quaternary ammonium compounds suitable as a fabric softening active in the present compositions include compounds of the formula:

wherein each R substituent is either hydrogen, a short chain $C_1$-$C_6$, preferably $C_1$-$C_3$ alkyl, e.g., methyl (most preferred), ethyl, propyl and the like, poly ($C_{2-3}$ alkoxy), preferably polyethoxy, group, benzyl, or mixtures thereof; each m is 2 or 3; each n is from 1 to about 4, preferably 2; each Y is —O—(O)C— or —C(O)—O and it is acceptable for each Y to be the same or different; the sum of carbons in each $R^1$, is $C_{11}$-$C_{21}$, preferably $C_{13}$-$C_{19}$, with each $R^1$ being a hydrocarbyl, or substituted hydrocarbyl group; it is acceptable for $R^1$ to be unsaturated or saturated and branched or linear and preferably it is linear; it is acceptable for each $R^1$ to be the same or different and preferably these are the same; and $X^-$ can be any softener-compatible anion, preferably, chloride, bromide, methylsulfate, ethylsulfate, sulfate, phosphate, and nitrate, more preferably chloride or methyl sulfate. Preferred diester quaternary ammonium compounds are typically made by reacting alkanolamines such as MDEA (methyldiethanolamine) with fatty acids. Some materials that typically result from such reactions include N,N-di(acyl-oxyethyl)-N,N-dimethylammonium chloride or N,N-di(acyl-oxyethyl)-N,N-dimethylammonium methylsulfate wherein the acyl group is derived from animal fats such as tallow, or vegetable oils such as palm or unsaturated, and polyunsaturated, fatty acids, e.g., oleic acid, and/or partially hydrogenated fatty acids, derived from vegetable oils and/or partially hydrogenated vegetable oils, such as, canola oil, safflower oil, peanut oil, sunflower oil, corn oil, soybean oil, tall oil, rice bran oil, etc. Non-limiting examples of suitable fatty acids are listed in U.S. Pat. No. 5,759,990 at column 4, lines 45-66. Non-limiting examples of preferred diester quats for the present invention include N,N-di(tallowoyloxyethyl)-N,N-dimethylammonium chloride (available from Akzo under the trade name Armosoft® DEQ) and N,N-di(canola-oyloxyethyl)-N,N-dimethylammonium chloride (available from Degussa under the trade name Adogen® CDMC).

Dialkyl Quaternary Ammonium Compounds (DQA)

The dialkyl quaternary ammonium compounds suitable as a fabric softening active in the present compositions include compounds of the formula:

wherein each R substituent is either hydrogen, a short chain $C_1$-$C_6$, preferably $C_1$-$C_3$ alkyl, e.g., methyl (most preferred), ethyl, propyl and the like, poly ($C_{2-3}$ alkoxy), preferably polyethoxy, group, benzyl, or mixtures thereof; each m is 2 or 3; each n is from 1 to about 4, preferably 2; each Y is $CH_2$, or —NR—C(O)—, or —C(O)—NR— and it is acceptable for each Y to be the same or different; the sum of carbons in each $R^1$, minus (n+1) when Y is $CH_2$, is $C_{12}$-$C_{22}$, preferably $C_{14}$-$C_{20}$, with each $R^1$ being a hydrocarbyl, or substituted hydrocarbyl group; it is acceptable for $R^1$ to be unsaturated or saturated and branched or linear and preferably it is linear; it is acceptable for each $R^1$ to be the same or different and preferably these are the same; and $X^-$ can be any softener-compatible anion, preferably, chloride, bromide, methylsulfate, ethylsulfate, sulfate, phosphate, and nitrate, more preferably chloride or methyl sulfate.

Additional Adjunct Fabric Softening Actives:

In one embodiment, the composition comprises an additional adjunct fabric softening active selected from the group consisting of: imidazolinium quaternary compounds, cationic starch, sucrose ester-based fabric care materials, cationic and aminosilicones, and mixtures thereof. Those of skill in the art will understand that the benefit agent (comprising said FSA) can include, in addition or alternatively, the additional fabric softening active in forming said plurality of particles where the additional fabric softening active has the requisite melting point and phase transition temperature in aqueous solution as defined above. Where the additional fabric softening active does not have the melting point and the phase transition temperature as defined herein, the benefit agent is free or essentially free of any additional fabric softening active. The level of additional fabric softening active can be provided such that the total amount of fabric softening active and additional fabric softening active is from about 1% to about 30%.

Imidazolinium Quaternary Compounds

In one embodiment, the additional adjunct fabric softening active comprise an imidazolinium quaternary compound of the following formula:

wherein each R, $R^1$, and $A^-$ have the definitions given above; each $R^2$ is a $C_{1-6}$ alkylene group, preferably an ethylene group; and G is an oxygen atom or an —NR— group.

Examples of imidazolinium quaternary compounds include: 1-methyl-1-tallowylamidoethyl-2-oleylimidazolinium methylsulfate and 1-methyl-1-oleylamidoethyl-2-oleylimidazolinium methylsulfate, wherein $R^1$ is an acyclic aliphatic $C_{15}$-$C_{17}$ hydrocarbon group, $R^2$ is an ethylene group, G is a NH group, $R^5$ is a methyl group and $A^-$ is a methyl sulfate anion, available commercially from Degussa under the trade names Varisoft® 475 and Varisoft® 3690, respectively.

Cationic Starch

In another aspect, the present invention provides a cationic starch as a fabric softening active. The term "cationic starch" is used herein in the broadest sense. In one aspect of the invention, cationic starch refers to starch that has been chemically modified to provide the starch with a net positive charge in aqueous solution at pH 3. This chemical modification includes, but is not limited to, the addition of amino and/or ammonium group(s) into the starch molecules. Non-limiting examples of these ammonium groups may include substitu- ents such as trimethylhydroxypropyl ammonium chloride, dimethylstearylhydroxypropyl ammonium chloride, or dimethyldodecylhydroxypropyl ammonium chloride. See Solarek, D. B., *Cationic Starches in Modified Starches: Properties and Uses*, Wurzburg, O. B., Ed., CRC Press, Inc., Boca Raton, Fla. 1986, pp 113-125. Cationic starch is described in U.S. Pat. Pub. 2004/0204337 A1, published Oct. 14, 2004, to Corona et al., at paragraphs 16-32.

Sucrose Ester-Based Fabric Care Materials

In another embodiment, the compositions of the present invention may comprise a sucrose ester-based fabric care material as a fabric softening active. A sucrose ester may be composed of a sucrose moiety having one or more of its hydroxyl groups esterified. Sucrose is a disaccharide having the following formula:

Alternatively, the sucrose molecule can be represented by the formula: $M(OH)_8$, wherein M is the disaccharide backbone and there are total of 8 hydroxyl groups in the molecule. Thus, sucrose ester can be represented by the following formula:

$$M(OH)_{8-x}(OC(O)R^1)_x$$

wherein x of the hydroxyl groups are esterified and (8−x) hydroxyl groups remain unchanged; x is an integer selected from 1 to 8, or from 2 to 8, or from 3 to 8, or from 4 to 8; and $R^1$ moieties are independently selected from $C_1$-$C_{22}$ alkyl or $C_1$-$C_{30}$ alkoxy, linear or branched, cyclic or acyclic, saturated or unsaturated, substituted or unsubstituted. In one embodiment, the $R^1$ moieties comprise linear alkyl or alkoxy moieties having independently selected and varying chain length. For example, $R^1$ may comprise a mixture of linear alkyl or alkoxy moieties wherein greater than 20% of the linear chains are $C_{18}$, or greater than 50% of the linear chains are $C_{18}$, or greater than 80% of the linear chains are $C_{18}$. In another embodiment, the $R^1$ moieties comprise a mixture of saturate and unsaturated alkyl or alkoxy moieties; the degree of unsaturation can be measured by "Iodine Value" (hereinafter referred as "IV", as measured by the standard AOCS method). The IV of the sucrose esters suitable for use herein ranges from 1 to 150, or from 2 to 100, or from 5 to 85. The $R^1$ moieties may be hydrogenated to reduce the degree of unsaturation.

In a further embodiment, the unsaturated $R^1$ moieties may comprise a mixture of "cis" and "trans" forms about the unsaturated sites. The "cis"/"trans" ratios may range from 1:1 to 50:1, or from 2:1 to 40:1, or from 3:1 to 30:1, or from 4:1 to 20:1. In another embodiment, the composition comprises an olyhydroxy material or sugar derivative. Polyhydroxy amide structures as disclosed in U.S. Pat. No. 5,534,197 by Scheibel et al. and U.S. Pat. No. 5,512,699 by Connor et al.; Pentaerythritol compounds and derivatives as disclosed in U.S. Pat. No. 6,294,516; cyclic polyols and/or reduced saccharides as disclosed in U.S. Pat. No. 6,410,501.

In still another embodiment, the compositions of the present invention may comprise cationic or amino functionalized silicones as a fabric softening active. Typical examples of cationic or amino functionalized silicones are those described in U.S. Pat. Appl. Publ. No. 2004/036319 and U.S. Pat. Publ. No. 2005/0026793 A1, Feb. 3, 2005, at paragraphs 137-162. In one embodiment, the aminosilicones can be linear or branched structured aminosilicone polymers comprised of the following base units:

wherein $R^1$, $R^2$, $R^3$ and $R^4$ can independently be (1) $C_1$-$C_{22}$ linear or branched, substituted or unsubstituted hydrocarbyl moiety, or (2) —O—$R^{11}$, —O—$R^{12}$, —O—$R^{13}$, and —O—$R^{14}$, where $R^{11}$, $R^{12}$ $R^{13}$, and $R^{14}$ are H or $C_1$-$C_{22}$ linear or branched, substituted or unsubstituted hydrocarbyl moiety. The nomenclature "$SiO_{n/2}$" means the ratio of oxygen atoms to silicon atoms, i.e., $SiO_{1/2}$ means one oxygen atom is shared between two silicon atoms. Likewise, $SiO_{2/2}$ means two oxygen atoms are shared between two silicon atoms and, $SiO_{3/2}$ means three oxygen atoms are shared between two silicon atoms.

L and K can independently be $C_1$-$C_{22}$ linear or branched, substituted or unsubstituted hydrocarbyl moiety. Preferably L and K are independently $C_1$-$C_{12}$ linear or branched, substituted or unsubstituted hydrocarbyl moiety. More preferably L and K are independently $C_1$-$C_4$ linear or branched, substituted or unsubstituted hydrocarbyl moiety. Most preferably L and K are independently methylene, ethylene, propylene, 2-methylpropylene, butylene, octadecylene, or 3-(2,2',6,6'-tetramethyl-4-oxy-piperidyl)propyl.

$R^5$, $R^6$, $R^7$ and $R^8$ can independently be H or $C_1$-$C_{22}$ linear or branched, substituted or unsubstituted hydrocarbyl moiety, including nitrogen and other heteroatom containing substituent. Preferably $R^5$, $R^6$, $R^7$ and $R^8$ are independently H or $C_1$-$C_{12}$ linear or branched, substituted or unsubstituted, alkyl or aryl hydrocarbyl moiety, including nitrogen containing substituent and oxygen containing substituent. Most preferably, $R^5$, $R^6$, $R^7$ and $R^8$ are independently H, phenyl, cyclohexyl, phenyl, 2-aminoethyl, 2-(N-2-aminoethyl)aminoethyl, 2-[N-2-(N-2-aminoethyl)aminoethyl]aminoethyl, 2-(N-phenyl)aminoethyl, 2-(N-cyclohexyl)aminoethyl, polyethyleneoxide, polypropyleneoxide, polyethyleneoxide-co-polypropyleneoxide, or polyethyleneoxide-co-polypropyleneoxide-co-polyethyleneamine.

Pearlescence Determination:

The liquid composition of the present invention has a pearlescent appearance.

Without wishing to be bound by theory, it is believed that pearlescence is produced by specular reflection of light. Light reflected from the plurality of particles in the benefit agent as they lie essentially parallel to each other at different levels in the composition creates a sense of depth and luster. Some light is reflected off the plurality of particles, and the remainder will pass through the particles. Light passing through the plurality of particles, may pass directly through or be refracted. Reflected, refracted light produces a different color, brightness and luster.

Without wishing to be bound by theory, the applicant believes that the plurality of particles, arranged at different levels in the composition, act to change the direction of the light. The extent and nature of this refraction of light is described by the Fresnel equations and results in color variation that changes with movement of the solution. This appearance can be described as gonioapparent.

It should be understood that those skilled in the art will know of other ways to describe pearlescent appearance. The description given here is just one non-limiting way of describing pearlescent appearance.

Formulations comprising pearlescing agents having pearlescent appearance are known and have been described in publications such as in WO 2007/111899. The present invention however, has unexpectedly achieved the important benefits of providing the desired pearlescent appearance without the need for added pearlescent agents. Indeed, the present invention has importantly found that pearlescent appearance can be achieved by controlling the size and structure of the benefit agent via the process as disclosed herein.

Liquid Composition

Depending upon the specific benefit agent, or mixtures thereof, which is present in the corresponding liquid composition, such composition may take various forms.

According to one preferred embodiment of the present invention, the composition may take a form selected from the group of hair dressing formulations, conditioners, hand and body lotions, skin moisturizing products, skin cleansing or disinfecting compositions, shampoos, shower gels, toilet milks, cream foundations, make-up removal compositions, sun and ultraviolet radiation protection lotions, skin care creams, anti-age preparations, anti-acne preparations, local analgesics, deodorants, antiperspirants, lipsticks, nail polishes, and combinations thereof.

According to a more preferred embodiment, the composition of the present invention may take a form selected from the group of fabric conditioning compositions, fabric softening compositions, fabric care compositions, fabric treatment compositions, and combinations thereof. More preferably, the composition of the present invention is selected from the group of fabric conditioning compositions and fabric softening compositions, even more preferably from the group of fabric softening compositions.

Optional Ingredients:

According to another aspect of the present invention, the fabric softening compositions may comprise one or more of the following optional ingredients: perfumes, blooming perfumes, perfume microcapsules, pro-perfumes, dispersing agents, stabilizers, pH control agents, metal ion control agents, colorants, optical brighteners, dyes, odor control agent, cyclodextrin, solvents, soil release polymers, preservatives, antimicrobial agents, chlorine scavengers, anti-shrinkage agents, fabric crisping agents, spotting agents, anti-oxidants, anti-corrosion agents, bodying agents, drape and form control agents, smoothness agents, static control agents, wrinkle control agents, sanitization agents, disinfecting agents, germ control agents, mold control agents, mildew control agents, antiviral agents, anti-microbials, drying agents, stain resistance agents, soil release agents, malodor control agents, fabric refreshing agents, chlorine bleach odor control agents, dye fixatives, dye transfer inhibitors, color maintenance agents, color restoration/rejuvenation agents, anti-fading agents, whiteness enhancers, anti-abrasion agents, wear resistance agents, fabric integrity agents, anti-wear agents, defoamers and anti-foaming agents, sud suppressors, electrolytes, preservatives, opacifiers, structurants, viscosity modifiers, deposition aids, fabric conditioning agents in solid form such as clay, emulsifiers, stabilizers, rinse aids, UV protection agents, sun fade inhibitors, insect repellents, anti-allergenic agents, enzymes, flame retardants, water proofing agents, fabric comfort agents, water conditioning agents, shrinkage resistance agents, stretch resistance agents, and mixtures thereof. These ingredients are described in further detail in EP 1297101 and in WO 01/85888 and the references cited therein; and in U.S. Pat. Appl. Pub. No. US 2003/0060390, at paragraphs 123-222. See also e.g. U.S. Pat. No. 4,157,307 to Jaeger et al., U.S. Pat. No. 5,942,217 to Woo et al., and U.S. Pat. No. 6,875,735 to Frankenbach et al. Additional suitable additives are known and can be included in the present formulation as needed. See e.g. U.S. Pat. Publ. No. 2004/0204337. In one embodiment, the liquid composition according to the present invention is free or substantially free of any of the aforementioned additives. As used herein, substantially free of a component means that no amount of that component is deliberately incorporated into the composition.

According to one preferred embodiment wherein the liquid composition is selected from fabric softening compositions, such compositions may further comprise adjunct fabric softening actives, as further optional ingredients. These active may include one or more of the following: silicones, including those described in U.S. Pat. Pub. No. 2002/0077265 A1, to Buzzacarini et al., published Jun. 20, 2002 at paragraphs 51-57; clays as described in U.S. Pat. Pub. No. 2004/0142841 A1, published Jul. 22, 2004, to de Buzzacarini et al., from paragraphs 74-99; fats and/or fatty acids as described in U.S. Pat. Appl. Pub. No. 2006/0122087 A1; polyhydroxy amide structures as described in U.S. Pat. No. 5,534,197 by Scheibel et al. and U.S. Pat. No. 5,512,699 by Connor et al.; Pentaerythritol compounds and derivatives thereof as disclosed in U.S. Pat. No. 6,294,516; and cyclic polyols and/or reduced saccharides as disclosed in U.S. Pat. No. 6,410,501.

Perfume Additive

One preferred optional ingredient according to the present invention is a perfume additive. As used herein "perfume additive" means any odoriferous material that is subsequently released into the aqueous bath and/or onto the surfaces contacted therewith. The perfume additives herein can be relatively simple in their compositions or can comprise highly sophisticated complex mixtures of natural and synthetic chemical components, all chosen to provide any desired odor. Nonlimiting examples of different perfume compositions are available in U.S. Pat. Publ. No. 2003/0104969A1 issued Jun. 5, 2003 to Caswell et al.; U.S. Pat. No. 5,714,137 issued Feb. 3, 1998 to Trinh et al.; and U.S. Pat. No. 6,048,830 issued Apr. 11, 2000 to Gallon et al.

In one embodiment, the perfume additive comprises a perfume microcapsule. Perfume microcapsules may include those described in the following references: U.S. Pat. Publ. Nos. 2003/215417 A1, 2003/216488 A1, 2003/158344 A1, 2003/165692 A1, 2004/071742 A1, 2004/071746 A1, 2004/072719 A1, 2004/072720 A1, 2003/203829 A1, 2003/195133 A1, 2004/087477 A1, 2004/0106536 A1; EP 1393706 A1; U.S. Pat. Nos. 6,645,479, 6,200,949, 4,882,220, 4,917,920, 4,514,461, 4,234,627 and U.S. RE 32,713. In one embodiment, the perfume microcapsule is a friable perfume microcapsule (versus, e.g., a water-activated perfume microcapsule). Friability refers to the propensity of the microcapsules to rupture or break open when subjected to direct external pressures or shear forces. For purposes of the present invention, the microcapsules utilized are "friable" if, while attached to fabrics treated therewith, they can be ruptured by the forces encountered when the capsule-containing fabrics are manipulated by being worn or handled (thereby releasing the contents of the capsule).

Aqueous Carrier

The compositions of the present invention will generally comprise an aqueous carrier comprising water. The level of aqueous carrier generally constitutes the balance of the present compositions, comprising from about 10% to about 95%, alternatively from about 20% to about 80%, alternatively from about 30% to about 70%, and alternatively from about 40% to about 60%, of said aqueous carrier by weight of said fabric enhancer.

In one preferred embodiment where the composition is a fabric softening composition, the composition of the present invention is free or substantially free of detersive surfactants. According to this one preferred embodiment, the composition comprises from up to 5% of a detersive surfactant, preferably up to 2%, more preferably up to 1%, most preferably up to 0.5%, by weight of the composition.

Viscosity

According to one aspect of the present invention, it has been surprisingly discovered that the presence of a plurality of particles having a sheet-like microstructure and having an average size ranging from 0.1 to 50 µm is not detrimental to the viscosity profile of the resulting liquid compositions. Accordingly, the compositions of the present invention exhibit commercially acceptable viscosity upon prolonged storage at ambient temperature. The expression "prolonged storage at ambient temperature" means 1 liter of a composition of the present invention is stored for 1 year to at about 21° C.

Figure 1:
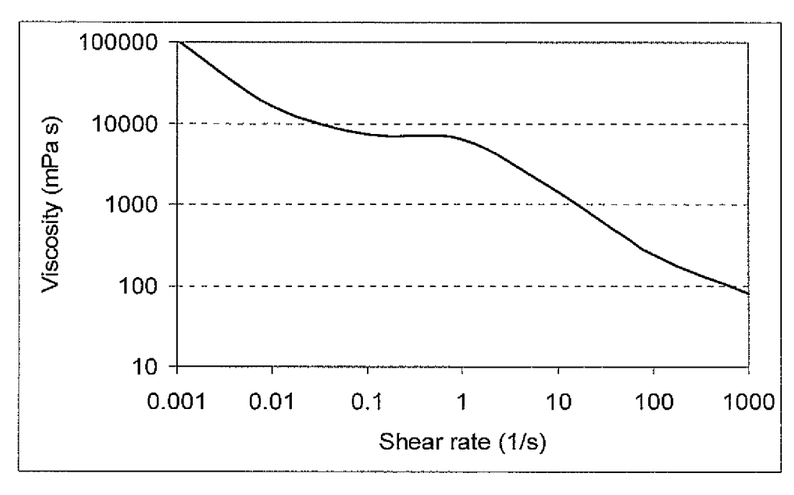
FIG. 1 shows a typical shear thinning viscosity profile at a temperature of 20° C. of the compositions according to the present invention.

FIG. 1 shows that typically, the compositions according to the present invention have a non-newtonian and shear thinning viscosity profile, when measured with an ANTON PAAR ASC Rheometer, at a temperature of 20° C.

In one embodiment, the viscosity of said composition is between about 0.1 mPas and about 1000000 mPas, preferably between about 1 mPas and about 100000 mPas, more preferably between about 10 mPas and about 100000 mPas, and most preferably between about 50 mPas and about 100000 mPas, when measured with an Anton Paar ASC equipment at a temperature of 20° C., and at a respective shear rate of 1000 s−1 and 0.001 s−1.

According to one preferred embodiment of the present invention where the composition is a liquid fabric softening composition, the liquid composition may be used in a so-called rinse process. Typically, such compositions are added during the rinse cycle of an automatic laundry washing machine. One aspect of the invention provides dosing the liquid softening composition of the present invention during the rinse cycle of an automatic laundry washing machine. Another aspect of the invention provides for a kit comprising a liquid composition of the present invention and optionally Process of Preparing a Liquid Composition Having Pearlescent Aesthetics In another embodiment, the present invention relates to a process of preparing a liquid composition having pearlescent aesthetics, wherein the composition comprises a benefit agent, the process comprising the steps of processing the benefit agent thereby producing a plurality of particles, the particles having a sheet-like microstructure and an average size ranging from 0.1 to 50 µm.

It has surprisingly been found that the compositions of the present invention can be manufactured using a process which involves cavitation within the composition generated by a high-shear homogenizer. As used herein, high-shear homogenizers include hydrodynamic cavitation reactors. Without intending to be bound by theory, it is believed that the hydrodynamic or ultrasonic cavitation and/or high shear causes sufficient disruption within the composition to create suitably sized particles having the desired sheet-like microstructure.

The process for manufacturing the present compositions comprises: providing one or two feeds into a pre-mixing chamber, where the feed(s) contains at least a benefit agent and a solvent, preferably an aqueous carrier; then exerting an energy density onto said feed from about 1 J/ml to about 50 J/ml to cause intense shear and cavitation within the feed within the mixing chamber to thereby produce a plurality of particles as above-described. Importantly, the feed(s) must be such that the benefit agent in a molten form must be introduced and contacted with the cold stream of aqueous carrier while being subjected to the high shear mixing within the mixing chamber. In one embodiment, the temperature of the benefit agent is from about 30° C. to about 120° C., preferably, 40° C. to about 100° C. and the temperature of the aqueous carrier is from about 0° C. to about 30° C., preferably from about 5° C. to about 25° C. Those of skill in the art will understand that the desired flow rates should be selected such that sufficient cooling occurs to bring at least a portion of the benefit agent below the melting point, thereby solidifying said portion of the benefit agent. In one embodiment, the ratio of flow rates between the benefit agent and the aqueous carrier is 1 to 2. In another embodiment, the ratio of flow rates between the benefit agent and the aqueous carrier is to 1:20. In a third embodiment, the ratio of flow rates between the benefit agent and the aqueous carrier is between any of the two previous embodiments. In one embodiment, the feeds are combined while being simultaneously while being subjected to high shear within the mixing chamber.

This process also involves the step of transferring heat from the benefit agent to the solvent. The benefit agent is cooled down whilst being sheared as a result of the energy density to which it is submitted. This process then includes the step of discharging the liquid composition at a flow rate from about 1 kg/min to about 1000 kg/min. In one embodiment, the feed is fed into said mixing chamber via an element forming an orifice. In one embodiment, the mixing chamber comprises a blade. It is believed that the process step of subjecting the feed to an energy density onto said feed from about 1 J/ml to about 50 J/ml causes cavitation within the composition traveling within the mixing chamber, causing sufficient disruption to the feed within the mixing chamber to cause the benefit agent to form a plurality of particles according to the present invention.

According to one preferred embodiment of the present invention, the feed as above-described, which is preferably an aqueous solution, is fed into the above-mentioned equipment at a temperature ranging from 0° C. to 80° C., preferably from 1° C. to 50° C., more preferably from 2° C. to 30° C., and most preferably from 3° C. to 15° C. According to another preferred embodiment, the one or the two feeds are fed into the above-mentioned equipment at a pressure ranging from 0 to 600 bar, preferably from 0 to 350 bar, more preferably from 50 to 150 bar, and most preferably from 75 to 125 bar.

In a preferred execution of the present invention wherein the feed is an aqueous solution, said aqueous solution preferably comprises some electrolytes. Preferably, the aqueous solution comprises from about 0% to about 10%, more preferably from about 0.05% to about 1%, even more preferably from about 0.05% to 0.50%, and most preferably from about 0.10% to 0.30%, of electrolyte by weight of said aqueous solution.

In one embodiment, the discharged liquid composition is further mixed with additional ingredients comprising: a perfume, a perfume microcapsule, an additional additive as defined above, and mixtures thereof. In another embodiment, the feed is introduced into the mixing chamber using a single feed, where the feed can be premixed and combined with water prior to introduction into the mixing chamber. In another embodiment, the feed is not pre-mixed before entering the mixing chamber. In a further embodiment, the feed is introduced into the mixing chamber using a dual feed with a first feed comprising said at least one benefit agent, additional ingredients, and mixtures thereof, and a second feed comprising water. In one embodiment one or more of the feeds are premixed.

Energy Density

Energy Density is generated by exerting a power density on the feed within the mixing chamber for a residence time. In one embodiment of the present invention, the step of cavitating said feed in said mixing chamber is performed having an energy density from about 1 J/ml to about 100 J/ml, alternatively from about 1 J/ml to about 50 J/ml, alternatively from about 5 J/ml to about 35 J/ml. Energy Density can be represented by the equation:

$$E = W * \Delta T$$

where E represents energy density, W represents power density, and $\Delta T$ represents residence time. As defined herein, residence time means the average amount of time a particle remains within the mixing chamber. Residence time is determined by calculating the cavity size divided by the flow rate of fabric enhancer out of the mixing chamber.

Power Density and Residence Time

The liquid compositions of the present invention require relatively higher power density than conventional high sheer mixing. For ultrasonic mixing or a hydrodynamic cavitation reactor as used herein, power density can be determined by:

$$W = \Delta P / \Delta T$$

where W is the Power Density, $\Delta P$ is the applied pressure within the mixing chamber, and $\Delta T$ is the residence time.

In one embodiment, the energy density is generated from a power density of from about 0.5 W/ml to about 100,000 W/ml, alternatively from about 50 W/ml to about 30,000 W/ml. It is observed that the minimum Power Density required to achieve the liquid composition according to the present invention is about 0.5 W/ml at 20 kHz. Where the power density is about 0.5 W/ml, the residence time is about 15 minutes; alternatively, where the power density is about 100,000 W/ml the residence time is about 5 milliseconds. In one embodiment, the residence time is from about 1 millisecond (ms) to about 1 second, alternatively from about 1 ms to about 100 ms, alternatively from about 5 ms to about 50 ms. Further, where the residence time is less than 1 minute, the power density needs to be greater than 10 W/ml. Where the residence time is less than 1 second, the power density needs to be greater than 500 W/ml. Alternatively, where the residence time is less than 10 ms, the power density needs to be greater than 50,000 W/ml.

After the feed is subjected to the requisite energy density (as generated from the above mentioned power density and residence time), the obtained liquid composition is discharged at a flow rate from about 1 kg/min to about 1000 kg/min, alternatively 10 kg/min to about 500 kg/min. Flow rate can be represented by the equation $Q = 30 A \sqrt{(\Delta P)}$, where Q=flow rate, A=orifice size, and $\Delta P$=pressure within the mixing chamber. As defined herein, orifice size is the orifice cross sectional area. In one embodiment, the orifice size is from about 0.0001 inches$^2$ to 0.1 about inches$^2$, alternatively 0.0005 inches$^2$ to 0.1 about inches$^2$.

Ultra-Sonic Mixing

In one embodiment, the device used to prepare the liquid composition of the present invention is an ultrasonic homogenizer. Without intending to be bound by theory, it is believed that ultrasonic homogenizers achieve particle size reduction by hydrodynamic and/or ultrasonic cavitation. Further, it is believed that ultrasonic homogenizers are capable of operating at higher power and energy densities compared to conventional high shear mixers. See e.g. U.S. Pat. Publ. Nos. 2002/0001613 A1 to Neimiec et al., and 2004/0014632 A1 to Howard et al., and U.S. Pat. No. 5,174,930 to Stainmesse et al. One non-limiting example of a suitable ultrasonic homogenizer is the Sonolator™, supplied by Sonic Corporation of Connecticut. The ultra-sonic homogenizer comprises a vibrating member which is capable vibrating in a wide in frequency range (e.g. from about 0.2 kHz to about 500 kHz). The frequency range for process according to the present invention ranges from about 10 kHz, alternatively from about 20 kHz to about 250 kHz, alternatively to about 50 kHz.

Using an ultra-sonic homogenizer, the power density is estimated by the pressure drop and the residence time over which the pressure releases. The energy density required to convert the feed into the fabric enhancer of the present invention is reached by controlling pressure applied to the feed.

In one embodiment, the ultra-sonic homogenizer comprises: a mixing chamber, said mixing chamber comprising an entrance, at least one inlet, and an outlet; and an element with an orifice therein, said element being located adjacent the entrance of said mixing chamber, wherein said element comprises portions surrounding said orifice, and at least some of said portions surrounding said orifice have a hardness of greater than that of cemented tungsten carbide, e.g. a Vickers hardness that is between about 20 and about 100 GPa. In another embodiment, the apparatus comprises a blade in said mixing chamber disposed opposite the element with an orifice therein, said blade having a leading edge, wherein the leading edge of said blade has a hardness of greater than that of cemented tungsten carbide, e.g. a Vickers hardness that is between about 20 and about 100 GPa. In yet another embodiment, said leading edge of said blade comprises: silicon nitride, titanium nitride, aluminum oxide, silicon carbide, titanium carbide, boron carbide, titanium diboride, boron oxide, rhenium diboride, cubic boron nitride, cubic BC2N, diamond-like carbon, diamond, composites of diamond and cubic boron nitride, and coatings of any of these materials, including diamond-coated materials and diamond-like carbon, and mixtures thereof. See U.S. Ser. No. 60/937,501, filed Jun. 28, 2007.

EXAMPLES

The following examples will further illustrate the present invention. The formulations below are made by combining the listed ingredients in the listed proportions (weight % unless otherwise specified).

TABLE 1

| Ingredients: | FORMULATIONS | | | |
|---|---|---|---|---|
| (% by weight) | I | II | III | IV |
| Quat[1] | 12.5% | 12.5% | 12.5% | 12.5% |
| Silicone Antifoam[2] | 0% | 0.008% | 0.008% | 0.008% |
| Hydrochloric acid | 0.012% | 0.012% | 0.014% | 0.014% |
| Calcium Chloride | 0.2% | 0.2% | 0.05% | 0.1% |
| Perfume | 0% | 0.5% | 0.5% | 0.5% |
| Dye (ppm) | 0 | 15 | 15 | 15 |
| Water | balance | balance | balance | balance |

[1]"Quat" refers to N,N-di(tallowoyloxyethyl)-N,N-dimethylammonium chloride, available from Degussa under the trade name of Adogen SDMC in a 15% isoproponal solution.
[2]MP10 from Dow Corning.

Preparation of the Compositions.

Compositions A, B, C, D, E and F are prepared according to the following general procedure: One stream containing molten Quat[1] and one stream containing an aqueous solution containing hydrochloric acid and Calcium Chloride, are both fed into a dual-feed Sonolator™. Specific equipment processing conditions that are used are shown in Table 2 below. The stream coming out of the Sonolator™ is then post-treated and finished with the ingredients as mentioned in Table 1, by simple addition of the corresponding ingredients.

TABLE 2

| | COMPOSITIONS | | | | | |
|---|---|---|---|---|---|---|
| Process conditions: | A | B | C | D | E | F |
| Quat Temperature (° C.) | 75 | 75 | 75 | 75 | 75 | 75 |
| Quat Pressure (bar) | 100 | 100 | 100 | 200 | 100 | 100 |
| Aqueous solution temperature (° C.) | 10 | 10 | 30 | 10 | 10 | 10 |
| Aqueous solution Pressure (bar) | 100 | 100 | 100 | 100 | 100 | 100 |
| Total ingredients Formulations | I | II | I | I | IV | III |

Compositions A and B are meant to exemplify compositions according to the present invention but are not necessarily used to limit or otherwise define the scope of the present invention. Compositions C, D, E and F are comparative examples. More specifically, compositions A and B are liquid compositions comprising a benefit agent in the form of a plurality of particles, wherein the particles have a sheet-like microstructure and an average size ranging from 0.1 to 50 μm. In contrast, compositions C to F are liquid compositions comprising a benefit agent in the form of a plurality of particles, wherein the particles do not have a sheet-like microstructure and an average size ranging from 0.1 to 50 μm.

Comparative Data

Compositions A to F prepared as above-indicated were visually observed. The external visual appearance of each of the compositions was ranked in accordance with the following standard: S means strongly pearlescent appearance; L means lightly pearlescent appearance; and N means no pearlescent appearance.

Phase stability of compositions A to F was also visually observed using the Shelf Storage Test as defined herein after: Compositions A to F are stored in a plastic container with lid for 4 weeks at a temperature of about 21° C. A phase stable composition as defined herein, is a composition which shows substantially no phase separation as measured by the Shelf Storage Test. The phase stability of each of the compositions was ranked in accordance with the following standard: PS means phase stable; and NPS means non phase stable.

At the end of the 4 weeks period, viscosity stability of compositions A to F is also measured by using a Brookfield LVF viscometer, 60 rpm, #2 spindle. A viscosity stable composition as defined herein, is a composition which shows substantially no viscosity increase as measured with a Brookfield LVF viscometer, and when compared to the initial viscosity. The viscosity stability of each of the compositions was ranked in accordance with the following standard: VS means viscosity stable; and NVS means non viscosity stable. Results obtained are shown in Table 3 below.

TABLE 3

| | COMPOSITIONS | | | | | |
|---|---|---|---|---|---|---|
| | A | B | C | D | E | F |
| Pearlescent appearance | S | S | N | N | N | N |
| Phase stability | PS | PS | NPS | NPS | NPS | NPS |
| Viscosity | VS | VS | NVS | NVS | NVS | NVS |

The above results clearly show that compositions according to the present invention (compositions A and B), i.e. compositions comprising a benefit agent in the form of a plurality of particles, wherein the particles have a sheet-like microstructure and an average size ranging from 0.1 to 50 μm, provide a strongly pearlescent appearance whereas compositions not according to the present (compositions C to F) provide no pearlescent effect. The above results also clearly show the improved phase and viscosity stability obtained with compositions according to the present invention, when compared to liquid compositions not according to the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process of preparing a liquid composition having pearlescent aesthetics, wherein said composition comprises a benefit agent comprising a fabric care active, said process comprising the steps of combining a feed stream of solvent, said solvent having a temperature between 0° C. and 30° C., and a feed stream of molten benefit agent having a melting temperature greater than the temperature of said stream of solvent in a mixing chamber, exerting an energy density onto said combined feeds from about 1 J/ml to about 50 J/ml within the mixing chamber to produce a plurality of particles comprising said fabric care softening active, said particles having a sheet-like microstructure and an average size ranging from 0.1 to 50 μm, wherein said fabric care active comprises a fabric softening active comprising a diester quaternary ammonium fabric softener.

2. The process according to claim 1, wherein said composition is essentially free of any additional pearlescing agent.

3. The process according to claim 1, wherein said process further comprises the steps of:

a. providing a feed into a mixing chamber, said feed comprising:
   i. said benefit agent above the melting point of the benefit agent; and
   ii. an aqueous carrier at a temperature below the temperature of the benefit agent;
b. subjecting said feed within said mixing chamber to an energy density from about 1 J/ml to about 50 J/ml thereby producing a composition comprising plurality of particles according to claim 1; and
c. discharging the composition obtained in step b) from said mixing chamber at a flow rate from about 1 kg/min to about 1000 kg/min, wherein the pressure drop across the mixing chamber is be between about 1 bar to about 500 bar.

4. The process according to claim 3, wherein the benefit agent is fed at a temperature between 30° C. and 120° C., and wherein the solvent is fed at a temperature between 0° C. and 30° C.

5. The process according to claim 4, wherein the relative weight ratios of the benefit agent to solvent are between 1 to 2 and 1 to 20.

6. The process according to claim 3, wherein said step of subjecting said feed to said energy density comprises exerting a power density from about 0.5 W/ml to about 100,000 W/ml at a frequency from about 10 kHz to about 500 kHz.

7. The process according to claim 3, wherein said step of providing said feed into said mixing chamber further comprises: passing said feed through an element forming an orifice comprising an orifice size from about 0.0005 inches$^2$ to about 0.1 inches$^2$.

8. The process according to claim 3, wherein said feed passing through said mixing chamber creates a residence time of from about 1 millisecond to about 1 second.

9. The process according to claim 1, wherein said fabric care active comprises a fabric softening active selected from the group consisting of N,N -di(hydrogenated tallowoyloxyethyl)-N,N -dimethylammonium chloride; N,N-di(tallowoyloxyethyl)-N,N-dimethylammonium chloride; di-hydrogenated tallow dimethyl ammonium chloride; ditallowdimethyl ammonium chloride; and mixtures thereof.

10. A liquid fabric care composition prepared by the process of claim 1.

11. The composition according to claim 10, wherein said fabric softening active is an N, N-di (acyl-oxyethyl) -N,N-dimethyl ammonium chloride or methyl sulfate salt and mixtures thereof.

12. The composition according to claim 11, wherein said fabric softening active comprises a fabric softening active selected from the group consisting of N,N-di(hydrogenated tallowoyloxyethyl)-N,N-dimethylammonium chloride; N,N -di(tallowoyloxyethyl)-N,N-dimethylammonium chloride; and mixtures thereof.

13. The composition according to claim 10, wherein said composition comprises from 1% to 30% by weight of the composition of said benefit agent.

14. The composition according to claim 10, which further comprises components selected from the group consisting of additional fabric softening actives, perfumes, stabilizers, colorants, brighteners, dyes, malodor control agents, preservatives, antimicrobial agents, anti-shrinkage agents, fabric crisping agents, bodying agents, drape and form control agents, smoothness agents, static control agents, wrinkle control agents, soil release agents, dye fixatives, dye transfer inhibitors, color maintenance agents, color restoration/rejuvenation agents, anti-fading agents, whiteness enhancers, anti-abrasion agents, wear resistance agents, fabric integrity agents, anti-foaming agents, rinse aids, UV protection agents, sun fade inhibitors, water proofing agents, fabric comfort agents, shrinkage resistance agents, stretch resistance agents, film-forming polymers, plasticizers, sequestering agents, thickening agents, waxes, and mixtures thereof.

15. The composition according to claim 10, wherein the viscosity of said composition is comprised between about 0.1 mPas and about 1,000,000 mPas, when measured with an Anton Paar ASC equipment at a temperature of 20° C., and at a respective shear rate of 1000 s−1 and 0.001 s−1.

* * * * *